(12) United States Patent
Attia et al.

(10) Patent No.: US 12,053,305 B2
(45) Date of Patent: Aug. 6, 2024

(54) PREDICTING TRANSIENT ISCHEMIC EVENTS USING ECG DATA

(71) Applicant: Mayo Foundation for Medical Education and Research, Rochester, MN (US)

(72) Inventors: Itzhak Zachi Attia, Rochester, MN (US); Paul A. Friedman, Rochester, MN (US); Samuel J. Asirvatham, Rochester, MN (US); Peter A. Noseworthy, Rochester, MN (US); Suraj Kapa, Rochester, MN (US); Francisco Lopez-Jimenez, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 313 days.

(21) Appl. No.: 17/709,566

(22) Filed: Mar. 31, 2022

(65) Prior Publication Data
US 2022/0218289 A1    Jul. 14, 2022

Related U.S. Application Data

(62) Division of application No. 16/221,214, filed on Dec. 14, 2018, now Pat. No. 11,317,872.
(Continued)

(51) Int. Cl.
*A61B 5/00*    (2006.01)
*A61B 5/346*   (2021.01)
(Continued)

(52) U.S. Cl.
CPC ............ *A61B 5/7275* (2013.01); *A61B 5/346* (2021.01); *A61B 5/366* (2021.01); *A61B 5/4064* (2013.01);
(Continued)

(58) Field of Classification Search
CPC ....... A61B 5/7275; A61B 5/346; A61B 5/366; A61B 5/4064; A61B 5/7264;
(Continued)

(56) References Cited

U.S. PATENT DOCUMENTS 11,317,872 B2    5/2022   Attia et al.
2003/0199727 A1  10/2003  Burke et al.
(Continued)

OTHER PUBLICATIONS

Salerno et al., "Early Elevation in Pump Power with the HeartMate II Left Ventricular Assist Device Does Not Predict Late Adverse Events," The Journal of Heart and Lung Transplantation, 32(4):S38-9, Apr. 2013.
(Continued)

*Primary Examiner* — Eugene T Wu
(74) *Attorney, Agent, or Firm* — Fish & Richardson P.C.

(57) ABSTRACT

Apparatuses and methods are provided to predict or diagnose an ischemic event, such as a stroke or a transient ischemic attack (TIA). A machine-learning model such as a neural network is generated that allows for recognition of an ECG consistent with an ischemic event. A system is trained and used to process a recording of ECG data from a patient to generate a prediction indicating a likelihood that the patient will experience a stroke. In other examples, a system is trained and used to process a recording of ECG data from a patient and detect an ischemic event for the patient who did not appear to have such an ischemic event.

7 Claims, 6 Drawing Sheets

Related U.S. Application Data (60) Provisional application No. 62/599,157, filed on Dec. 15, 2017.

(51) Int. Cl.
| | | |
|---|---|---|
| *A61B 5/366* | (2021.01) | |
| *G06N 3/08* | (2023.01) | |
| *G16H 50/20* | (2018.01) | |
| *G16H 50/30* | (2018.01) | |
| *A61B 5/024* | (2006.01) | |
| *A61B 5/35* | (2021.01) | |

(52) U.S. Cl.
CPC .......... *A61B 5/7264* (2013.01); *A61B 5/7267* (2013.01); *A61B 5/7285* (2013.01); *G06N 3/08* (2013.01); *G16H 50/20* (2018.01); *G16H 50/30* (2018.01); *A61B 5/0006* (2013.01); *A61B 5/02405* (2013.01); *A61B 5/35* (2021.01); *A61B 5/7282* (2013.01)

(58) Field of Classification Search
CPC ... A61B 5/7267; A61B 5/7285; A61B 5/0006; A61B 5/02405; A61B 5/35; A61B 5/7282; G06N 3/08; G06N 3/045; G06N 3/084; G16H 50/20; G16H 50/30

See application file for complete search history.

(56) References Cited

U.S. PATENT DOCUMENTS

| | | |
|---|---|---|
| 2010/0222632 A1 | 9/2010 | Poirier |
| 2010/0305692 A1 | 12/2010 | Thomas et al. |
| 2011/0313238 A1 | 12/2011 | Reichenbach et al. |
| 2012/0078031 A1 | 3/2012 | Burke et al. |
| 2016/0091499 A1* | 3/2016 | Sterling ................. G16B 40/20 506/9 |
| 2018/0153476 A1* | 6/2018 | Annoni .................. G16H 50/30 |
| 2018/0153477 A1 | 6/2018 | Nagale et al. |
| 2018/0249967 A1 | 9/2018 | Lederman et al. |
| 2018/0353084 A1 | 12/2018 | Wainright et al. |
| 2019/0183431 A1 | 6/2019 | Attia et al. |

OTHER PUBLICATIONS

Trivedi et al., "Novel Thrombosis Risk Index as Predictor of Left Ventricular Assist Device Thrombosis," Asaio J., 59(4):380-3, Jul.-Aug. 2013.

* cited by examiner

PREDICTING TRANSIENT ISCHEMIC EVENTS USING ECG DATA

CROSS-REFERENCE TO RELATED APPLICATIONS

This application is a divisional of U.S. application Ser. No. 16/221,214, filed Dec. 14, 2018, which claims the benefit of U.S. Provisional Application Ser. No. 62/599,157, filed Dec. 15, 2017. The disclosures of the prior applications are considered part of (and are incorporated by reference in) the disclosure of this application.

BACKGROUND

Ischemic events, such as stroke, transient ischemic attack (TIA), and cerebrovascular accidents, can be devastating leaving residual neurologic deficits and disability. A patient who has a single transient ischemic event has a high risk for recurrence. Recently, it has been demonstrated that percutaneous interventions in patients who are having acute strokes can salvage brain tissue and lower morbidity and mortality. A major limitation, however, is failure to adequately recognize and respond to symptoms when they occur if there may be ambiguity. Therefore, an inexpensive, unobtrusive, easy to utilize test that can rapidly identify an impending or early onset of a stroke would be of great clinical value.

SUMMARY

This specification generally describes systems, methods, devices, and other techniques for predicting or diagnosing an ischemic event, such as a stroke or a transient ischemic attack (TIA). A machine-learning model such as a neural network can be generated that allows for recognition of an ECG consistent with an ischemic event. For example, a system employing a machine-learning model can be trained with a large training set of ECG data for known patients with and without ischemic events (e.g., acute stroke events) and can be used to process a recording of ECG data from a patient to generate a prediction indicating a likelihood that the patient will experience a stroke. The prediction can further indicate a likelihood that the subject mammal will experience the ischemic event within a pre-defined time interval from a time when the ECG recording was made. In other examples, a system employing a machine-learning model can be trained to diagnose an ischemic event for a patient who did not appear to have such an ischemic event, based on a recording of ECG data. The diagnosis can indicate a likelihood that the subject mammal experienced the ischemic event.

In some implementations, an ECG signal is provided as input to a machine-learning model (e.g., a deep neural network or a capsule network). During a training phase for the model, a corpus of training samples ECG signals of individuals are processed, enabling the model to learn characteristics of the ECGs that indicate a likelihood of stroke. For a predictive model that predicts the likelihood that a patient will experience a stroke within a certain period of time (e.g., 1, 2, 5, or 10 years), the ECG samples can be labeled with a binary indicator representing whether the patient whose ECG is represented in the training sample did or did not experience a stroke (or other ischemic event) within that period of time. For a detection model (also referred to as "diagnostic" model) that generates a prediction indicating whether an individual has recently experienced a stroke (or other ischemic event), the training samples include some samples representing ECG signals for patients who have not experienced a stroke and labels indicating the same, and other samples representing ECG signals for patients who have recently experienced a stroke and labels indicating the same. Machine-learning techniques such as backpropagation of errors with gradient descent can be used to train the model.

In some implementations, the model processes an ECG of the same patient at different time points so that the model can find patterns in the signals that show a progression of a central nervous system ischemic event. This may help identify early warning signs, as well as to delineate the natural evolution of electrocardiographic signals in the setting of brain ischemia.

In some implementations, specific ECG algorithms or models can be learned using handcrafted or manually identified features of the electrocardiogram, which could include the slopes of different waves, amplitude area, and center of gravity. These features can be used for linear and nonlinear estimation and classification to achieve the goals mentioned above.

In some implementations, an electrocardiographic signal can be obtained at baseline with a known normal/absent classification of acute neurologic ischemic event. Serial ECGs over time for the same individual can be used to determine the development of an ischemic event.

For any of the discussed implementations, the ECG signal may be from various sources including short 10-second, 12-lead signals, single lead recordings derived from limb or chest leads, or other combinations.

In some implementations, electrocardiographic recordings can be obtained by placing electrodes on the scalp, on the forehead, around the neck, or other head and neck regions to include electrocardiographic brain signals as well as cardiac signals, which may be used in combination to determine the presence of brain ischemia.

Some aspects of the subject matter disclosed herein include a method for predicting an ischemic event. The method can include receiving, by an ischemic event prediction neural network, a first neural network input, where the first neural network input representing an electrocardiogram (ECG) recording of a subject mammal, and processing, with the ischemic event prediction neural network, the first neural network input with a neural network to generate a prediction of an ischemic event for the subject mammal. The prediction may indicate a likelihood that the subject mammal will experience the ischemic event within a pre-defined time interval from a time when the ECG recording was made.

In certain examples, the ischemic event prediction neural network is trained on ECG training data that includes a plurality of ECG training samples, Each ECG training sample may include an ECG recording of a given mammal and a label indicating whether the given mammal is known to have experienced an ischemic event within the pre-defined time interval from the time when the ECG recording was made.

In certain examples, the given mammals for particular ones of the ECG training samples are different from each other.

In certain examples, for each of at least a subset of the ECG training samples, the label for the training sample or a second label for the training sample indicates an amount of time that elapsed between a time when the ECG recording for the training sample was made and a time when the given mammal for the training sample experienced an ischemic event.

In certain examples, the prediction of the ischemic event for the subject mammal further indicates an anticipated timing of the ischemic event.

In certain examples, the ischemic event is a transient ischemic attack (TIA). In certain examples, the ischemic event is a stroke.

In certain examples, the pre-defined time interval is in the range of 1-10 years.

In certain examples, at least two of the ECG training samples include ECG recordings of a same mammal taken at different times. The ECG training data may further describe a change between the ECG recordings of the same mammal taken at different times.

In certain examples, the ECG recording of the subject mammal was recorded over a first time interval. In certain examples, the method may further include obtaining a second neural network input. The second neural network input represents a second ECG recording of the subject mammal that was recorded over a second time interval. The first time interval and the second time interval are separated by a third time interval. The method may further include processing the first neural network input along with the second neural network input with the ischemic event prediction neural network to generate the prediction of the ischemic event for the subject mammal.

Some aspects of the subject matter disclosed herein include a method for diagnosing an ischemic event for a subject mammal. The method can include receiving, by an ischemic event detection neural network, a neural network input, where the neural network input represents an electrocardiogram (ECG) recording of the subject mammal that was recorded over a period of time. The subject mammal may have had no appearance of the ischemic event over the period of time. The method can further include processing, with the ischemic event detection neural network, the neural network input to determine a likelihood that the subject mammal experienced the ischemic event.

In certain examples, the ischemic event detection neural network is trained on ECG training data that includes a plurality of ECG training samples. Each ECG training sample includes an ECG recording of a given mammal and a label indicating whether the given mammal is known to have experienced an ischemic event.

In certain examples, the given mammals for particular ones of the ECG training samples are different from each other.

In certain examples, for each of at least a subset of the ECG training samples, the label for the training sample or a second label for the training sample indicates an amount of time that elapsed between a time when the ECG recording for the training sample was made and a time when the given mammal for the training sample experienced an ischemic event.

In certain examples, the ischemic event is a transient ischemic attack (TIA). In certain examples, the ischemic event is a stroke.

In certain examples, the ECG recording of the subject mammal was recorded over a first time interval. In certain examples, the method can further include obtaining a second neural network input. The second neural network input represents a second ECG recording of the subject mammal that was recorded over a second time interval which is separated from the first time interval by a third time interval. The method further includes processing the first neural network input along with the second neural network input with the ischemic event detection neural network to determine the likelihood that the subject mammal experienced the ischemic event.

These aspects and others can be implemented on a system having a data processing apparatus, e.g., which can include one or more computers in one or more locations. In some implementations, one or more computer-readable media have instructions stored thereon that, when executed by data processing apparatus, cause the data processing apparatus to perform this and other computer-based methods or processes described herein.

Some aspects of the subject matter disclosed herein include a computing system for predicting an ischemic event. The system can include one or more processors, and one or more computer-readable media having instructions stored thereon that, when executed by the one or more processors, cause performance of operations including receiving, by an ischemic event prediction neural network, a first neural network input, where the first neural network input representing an electrocardiogram (ECG) recording of a subject mammal, and processing, with the ischemic event prediction neural network, the first neural network input with a neural network to generate a prediction of an ischemic event for the subject mammal. The prediction can indicate a likelihood that the subject mammal will experience a stroke within a pre-defined time interval from a time when the ECG recording was made.

In certain examples, the ischemic event prediction neural network is trained on ECG training data that includes a plurality of ECG training samples. Each ECG training sample can include an ECG recording of a given mammal and a label indicating whether the given mammal is known to have experienced an ischemic event within the pre-defined time interval from the time when the ECG recording was made.

In certain examples, for each of at least a subset of the ECG training samples, the label for the training sample or a second label for the training sample indicates an amount of time that elapsed between a time when the ECG recording for the training sample was made and a time when the given mammal for the training sample experienced an ischemic event.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This specification generally describes systems, methods, devices, and other techniques for predicting or diagnosing an ischemic event, such as a stroke or a transient ischemic attack (TIA). Such systems, methods, devices, and other techniques can use neural networks or other machine-learning models.

Figure 1:
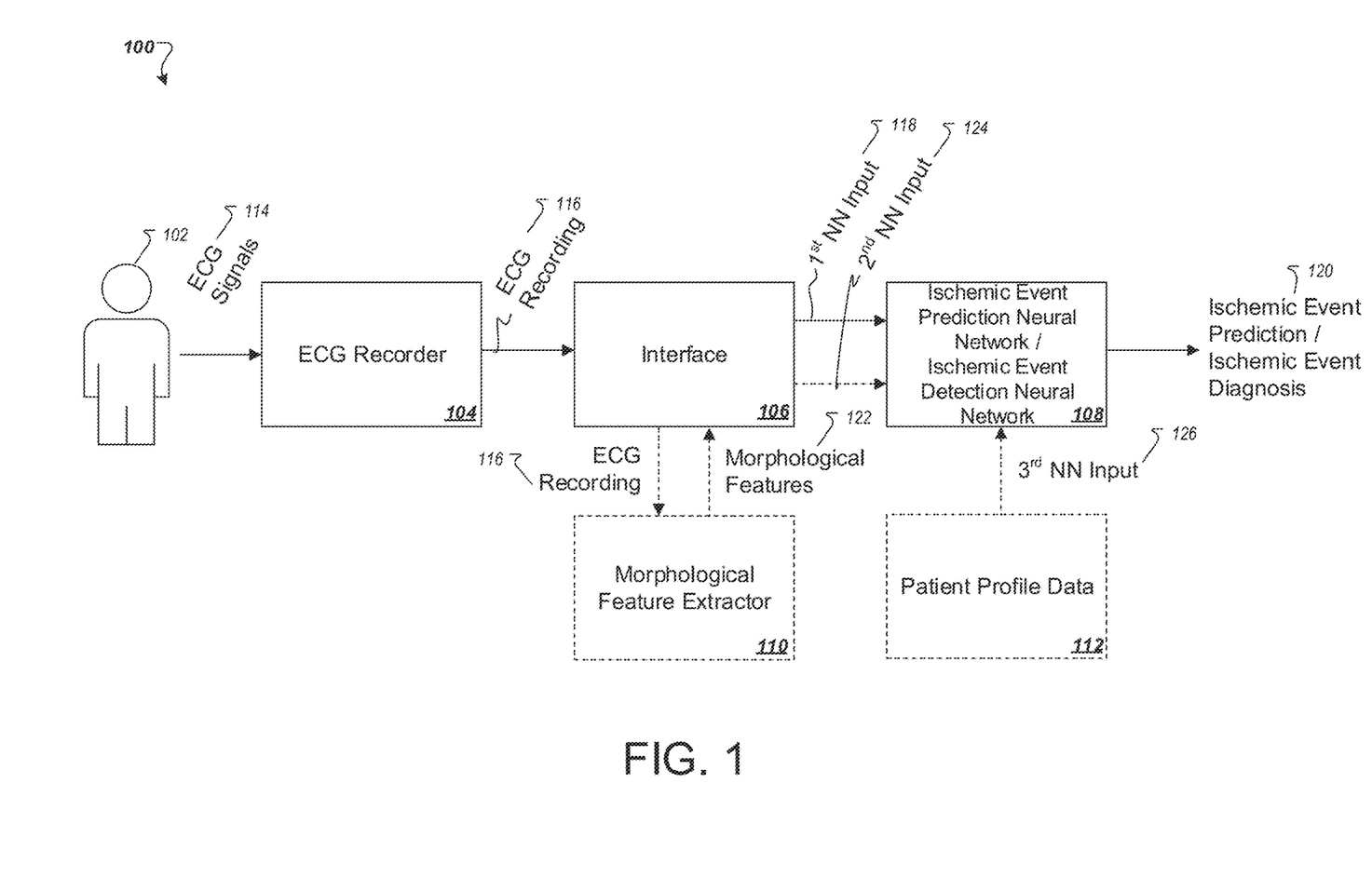
FIG. 1 is a diagram of an example system for ECG recording and ischemic event prediction or detection (e.g., diagnosis).

Referring to FIG. 1, a diagram is shown of an example system 100 for recording an ECG signal, and for predicting or diagnosing an ischemic event. The system 100 is configured to record an ECG of a patient 102 and to process the recording and, optionally, additional (auxiliary) data to generate an ischemic event prediction/diagnosis 120. Ischemic events include diseases resulting from a restriction in blood supply to tissues, causing a shortage of oxygen that is needed for cellular metabolism. Examples of ischemic events include a stroke and a transient ischemic attack (TIA). The system 100 is particularly advantageous to predict or diagnose an ischemic event that is not apparent or identifiable by conventional methods, devices, or techniques.

The patient 102 can be a human or any other mammal for which an ischemic event prediction or diagnosis is desired. To obtain an ECG recording of the patient 102, one or more electrodes are brought into contact with a surface of the patient's body. The electrodes can be arranged according to a standard 12-lead ECG configuration, or in other known configurations. The electrodes may or may not be affixed to the patient 102. In some implementations, fewer than 12-leads are provided to obtain the ECG. For example, a single-lead smartphone-based ECG sensor may be employed to sense the patient's ECG based on finger contact, or a patch with an electrode array may be affixed to the patient's chest.

The ECG recorder 104 includes hardware and/or software for sensing and capturing ECG signals 114 from the electrodes in contact with the patient 102. For example, the signals 114 may be filtered, amplified, and digitally sampled by a ECG recorder 104, and a ECG recording 116 can be generated that represents the patient's ECG for each available lead over a period of time. Typically, the recording 116 may be made based on a relatively short period of measurement. For example, a relatively short sample corresponding to just a few beats may be all that is required to be captured for purposes of making a prediction or diagnosis. In some implementations, a minimum recording time may be specified that is less than or equal to ten minutes, five minutes, one minute, forty-five seconds, thirty seconds, fifteen seconds, ten seconds, or five seconds. The ECG can be recorded while the patient 102 is in the supine position or other positions that correspond to positions of the patients whose ECGs were used as training examples for the system.

An interface 106 can be implemented on a computer or other data processing apparatus. The interface 106 receives a digitized ECG recording 116 from the ECG recorder 104 and processes the recording 116 to generate a first neural network input 118. The first neural network input 118 is a representation of the ECG recording that is suitable for processing by an ischemic event prediction/detection neural network 108. The first neural network input 118, for example, can identify values of the ECG signal level for each lead over the full recording time or over a subset of the recording time (e.g., a time interval that corresponds to a single heartbeat). The first neural network input 118 can represent the ECG recording for one or more individual beats or can represent an averaged beat based on ECG recordings from several measured beats.

The ischemic event prediction/detection neural network 108 is configured to process the first neural network input 118 and to generate ischemic event prediction/diagnosis 120 based on the first neural network input 118. The neural network 108 can include multiple layers of operations that have been trained to predict an ischemic event condition of a patient based on ECG recordings of the patient. In some implementations, two different neural networks 108 are created for ischemic event prediction and ischemic event detection, respectively. In other implementations, a single neural network 108 is created for both of the prediction and detection. The output 120 can indicate, for example, a likelihood that the patient 102 will experience an ischemic event within a pre-defined period of time (e.g., a time period selected from the range of 1-10 years). In some implementations, the output 120 can indicate a predicted length of time (e.g., a number of months or years) before the patient 102 has at least a threshold likelihood of experiencing an ischemic event. In some implementations, the output 120 can indicate a likelihood that the patient 102 has ever or has recently experienced an ischemic event (e.g., a detection/diagnosis score). The network 108 can be configured to generate a prediction or diagnosis for one or more particular types of ischemic events, such as a transient ischemic attack.

Neural networks are machine-learning models that employ multiple layers of operations to predict one or more outputs from one or more inputs. Neural networks typically include one or more hidden layers situated between an input layer and an output layer. The output of each layer is used as input to another layer in the network, e.g., the next hidden layer or the output layer. Each layer of a neural network specifies one or more transformation operations to be performed on input to the layer. Some neural network layers have operations that are referred to as neurons. Often, each neuron can receive one or more inputs and generates an output that is received by another neural network layer. The transformation operations of each layer can be carried out by one or more computers at one or more locations having installed software modules that implement the transformation operations.

The neural network 108 can be a feedforward neural network, a recurrent neural network, a convolutional neural network, a capsule network, or may include various portions having different characteristics, such as feedforward layers, recurrent layers, and/or convolutional layers. The ischemic event prediction/detection neural network 108 can be implemented on one or more computers or other data processing apparatus in one or more locations. The network 108 may be implemented on a smartphone or other personal device (e.g., tablet, desktop or notebook computer) in the same location as the patient 102, or may be implemented on one or more remote servers in communication with the interface 106.

In some implementations, the ischemic event prediction/detection neural network 108 is configured to process additional (auxiliary) information in generating ischemic event prediction/diagnosis 120. For example, the network 108 may process a second neural network input 124 in addition to the first neural network input 118 to generate ischemic event prediction/diagnosis 120.

Figure 6:
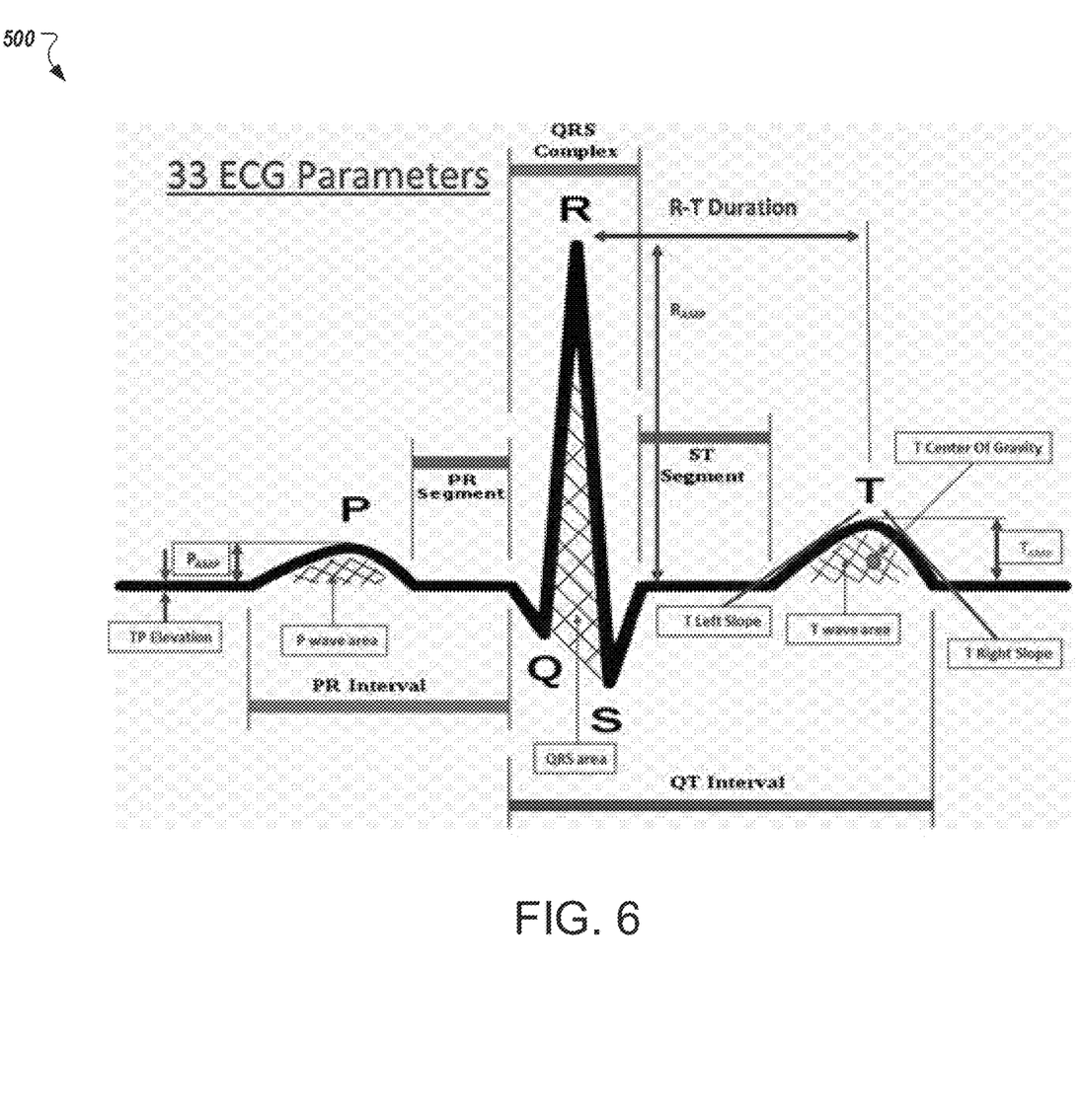
FIG. 6 is an example diagram of a segment of an ECG recording for a patient.

In some implementations, the second neural network input 124 represents morphological features 122 of the patient's ECG. FIG. 6, for instance, depicts a waveform or tracing 500 for a single beat from a patient's ECG. The waveform includes several segments including a P-wave, a QRS-complex, and a T-wave. The interface 106 can provide the ECG recording 116 to a morphological feature extractor 110 for analysis, and the extractor 110 can measure various morphological features 112 of one or more beats (or a composite or averaged beat) from the ECG recording 116. The morphological features 112 are parameters that describe attributes of the shape of the beat, including attributes of individual segments of the beat and attributes between segments. A number of morphological features that may be employed for ischemic event prediction/diagnosis are labeled in FIG. 6, such as a duration of the QRS-complex, am amplitude of the P-wave, R-wave, or T-wave, an area of the P-wave, QRS-complex, or T-wave, slopes of any of the waves, distances between the waves, and centers-of-gravity of the waves. The morphological feature extractor 110 provides values for the morphological features 122 to the interface 106, and the interface 106 formats them into an acceptable form for processing by ischemic event prediction/detection neural network 108 as second neural network input 124. The ischemic event prediction/detection neural network 108 processes the first and second inputs 118, 124 to generate ischemic event prediction/diagnosis 120.

In some implementations, the neural network 108 processes one or more third neural network inputs 126 representing patient profile data from a database 112. The patient profile data is another form of auxiliary information, and in particular it indicates non-ECG descriptions of the patient 102. For example, the third neural network inputs 126 representing patient profile data can include indications of one or more of age, weight, or sex of the patient 102, and/or other attributes of the patient 102. The ischemic event prediction/detection neural network 108 can process the first neural network input 118 and none, one, or both of second neural network input 124 and third neural network input 126 to generate ischemic event prediction/diagnosis 120.

The ischemic event prediction/detection neural network 108 outputs ischemic event prediction/diagnosis 120. In some implementations, the ischemic event prediction/detection neural network 108 is created and trained as an ischemic event prediction neural network 108 that generates an ischemic event prediction 120 based at least in part on the first neural network input 118 describing the ECG recording 116 of the patient. Alternatively, the ischemic event prediction/detection neural network 108 is created and trained as an ischemic event detection neural network 108 that generates an ischemic event detection 120 for a patient who has no significant appearance of an ischemic event, based at least in part on the first neural network input 118 describing the ECG recording 116 of the patient.

In embodiments where the ischemic event prediction/detection neural network 108 operates as an ischemic event prediction neural network 108, the ischemic event prediction 120 can indicate a likelihood that the patient 102 will experience an ischemic event within a pre-defined time interval from a time when the ECG recording was made. The pre-defined time interval can be in the range of 1-10 years. The pre-defined time interval can be less than 1 year, or more than 10 years. In some embodiments, the prediction 120 can further indicate an anticipated timing of the ischemic event.

The prediction 120 can be expressed as a probability or confidence score representing a probability or confidence that the patient 102 will experience an ischemic event within a pre-defined time from a time when the ECG recording was obtained. In some implementations, the prediction 120 is expressed as a selection of a particular classification from multiple possible classifications that represents a most likely condition of the patient 102. For example, a binary classification can be made indicating whether there is at least a threshold probability or confidence level that the patient 102 will experience an ischemic event within a pre-defined time. The ischemic event prediction 120 can identify this binary classification. As another example, the ischemic event prediction 120 can indicate a recommendation or selection of a monitoring or treatment option for the patient 102 based on a likelihood of the patient 102 being susceptible to development of an ischemic event. Thresholds used for any decision boundaries can be extracted from retrospective analysis and can be presented with positive and negative predictive value (PPV and NPV).

In alternative embodiments where the ischemic event prediction/detection neural network 108 operates as an ischemic event detection neural network 108, the ischemic event detection 120 can indicate a likelihood that the patient has experienced an ischemic event while the patient has no significant appearance of such an ischemic event.

Figure 2:
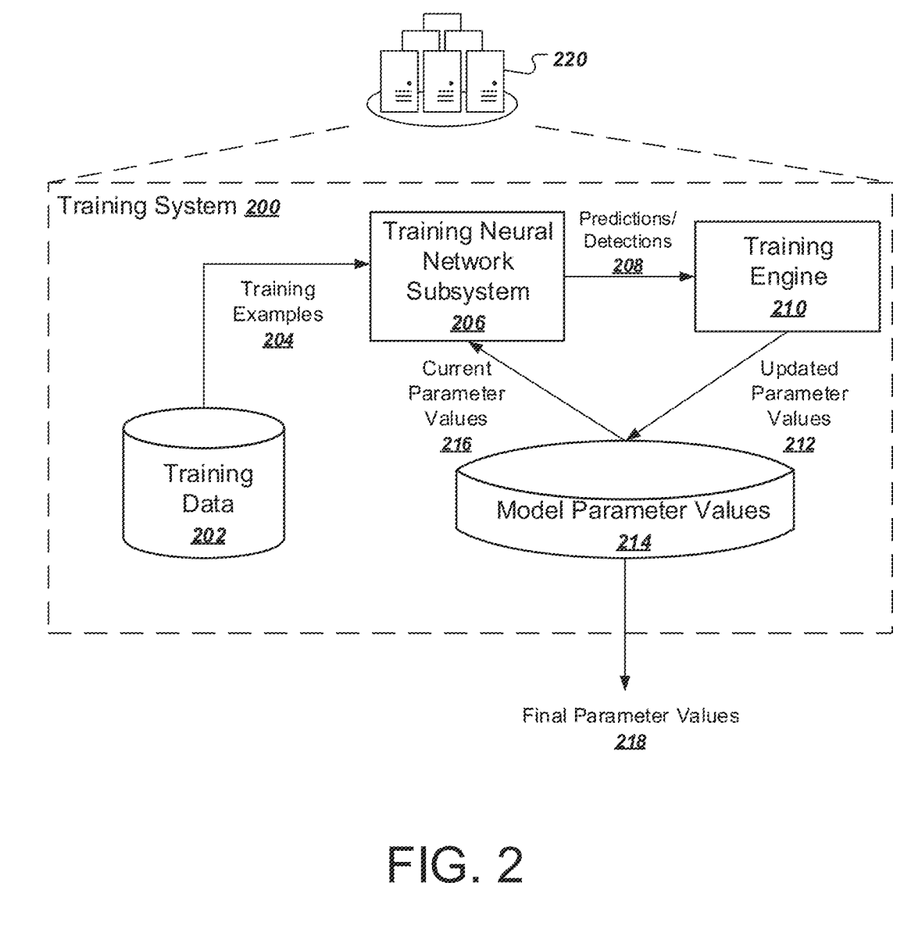
FIG. 2 depicts an example system for training an ischemic event prediction neural network or an ischemic event detection neural network.

FIG. 2 depicts an example system 200 for training an ischemic event prediction/detection neural network 108. The training system 200 can be hosted within a data center 220 which can be a distributed computing system having hundreds or thousands of computers in one or more locations.

The training system 200 includes a training neural network subsystem 206 that can implement the operations of each layer of a neural network that is designed to make an ischemic event prediction 120 or an ischemic event detection 120 from ECG recordings and, optionally, auxiliary information such as morphological features and patient profile data. The training neural network subsystem 206 includes a plurality of computing devices having software or hardware modules that implement the respective operations of each layer of the neural network according to an architecture of the neural network. Generally, the training neural network subsystem 206 has the same architecture as the ischemic event prediction neural network 108 or the ischemic event detection neural network 108. However, the training system 200 need not use the same hardware to compute the operations of each layer. In other words, the training system 200 can use CPUs only, highly parallelized hardware, or some combination of these.

The training neural network subsystem 206 can compute the operations of each layer of the training neural network subsystem 206 (or the ischemic event prediction/detection neural network 108) using current parameter values 216 stored in a collection of model parameter values 214. Although illustrated as being logically separated, the model parameter values 214 and the software or hardware modules performing the operations may actually be located on the same computing device or on the same memory device.

The training neural network subsystem 206 can generate, for each training example 204, an ischemic event prediction 208 or an ischemic event detection 208. A training engine 210 analyzes the predictions or detections 208 and compares the predictions or detections 208 to labels in the training examples 204 that indicate target predictions or detections for each training example 204. The training engine 210 then generates updated model parameter values 214 by using an appropriate updating technique, e.g., stochastic gradient descent with backpropagation. The training engine 210 can then update the collection of model parameter values 214 using the updated model parameter values 212. For example, each training example 204 can include a first component representing a single- or multi-lead ECG recording of a patient and a label indicating a target ischemic event prediction or detection. The first component can represent an ECG of a patient, and the label can indicate whether that particular patient is known to have actually experienced ischemic event. In this way, the neural network 108 can be trained using ECGs obtained in patients with known and validated ischemic event versus patients with no known ischemic event. The training examples can also include additional components representing morphological features or patient profile data, for example.

Referring back to FIG. 1, in embodiments where the ischemic event prediction/detection neural network 108 operates as an ischemic event prediction neural network 108, the training neural network subsystem 206 for the ischemic event prediction neural network 108 can be trained on ECG training data that includes a plurality of ECG training samples. Each of the ECG training samples includes an ECG recording of a given patient and a label indicating whether the given patient is known to have experienced an ischemic event within the pre-defined time interval from the time when the ECG recording was obtained. The ECG training data can be obtained from a plurality of patients. In some implementations, for one or more of the ECG training samples, the label for the training sample can further indicate an amount of time that elapsed between a time when the ECG recording for the training sample was made and a time when the given patient for the training sample experienced an ischemic event. Alternatively, this label information can be included in the ECG training sample as a second label in addition to the ECG recording and the label that indicates whether the given patient is known to have experienced an ischemic event within the pre-defined time interval from the time when the ECG recording was obtained.

In alternative embodiments where the ischemic event prediction/detection neural network 108 operates as an ischemic event detection neural network 108, the training neural network subsystem 206 for the ischemic event detection neural network 108 is trained on ECG training data that includes a plurality of ECG training samples. Each of the ECG training samples includes an ECG recording of a given patient and a label indicating whether the given patient is known to have experienced an ischemic event. The ECG training data can be obtained from a plurality of patients. In some implementations, for one or more of the ECG training samples, the label for the training sample can further indicate an amount of time that elapsed between a time when the ECG recording for the training sample was made and a time when the given patient for the training sample experienced an ischemic event. Alternatively, this label information can be included in the ECG training sample as a second label in addition to the ECG recording and the label that indicates whether the given patient is known to have experienced an ischemic event.

In some implementations, at least two of the ECG training samples include ECG recordings of a same patient which were obtained at different times. The ECG training data can further describe a change between the ECG recordings of the same patient that were taken at such different times.

After training is complete, the training system 200 can provide a final set of parameter values 218 to the system 100 for use in making ischemic event predictions or detections 120. The training system 200 can provide the final set of model parameter values 218 by a wired or wireless connection to the system 100 and neural network 108, for example.

Figure 3:
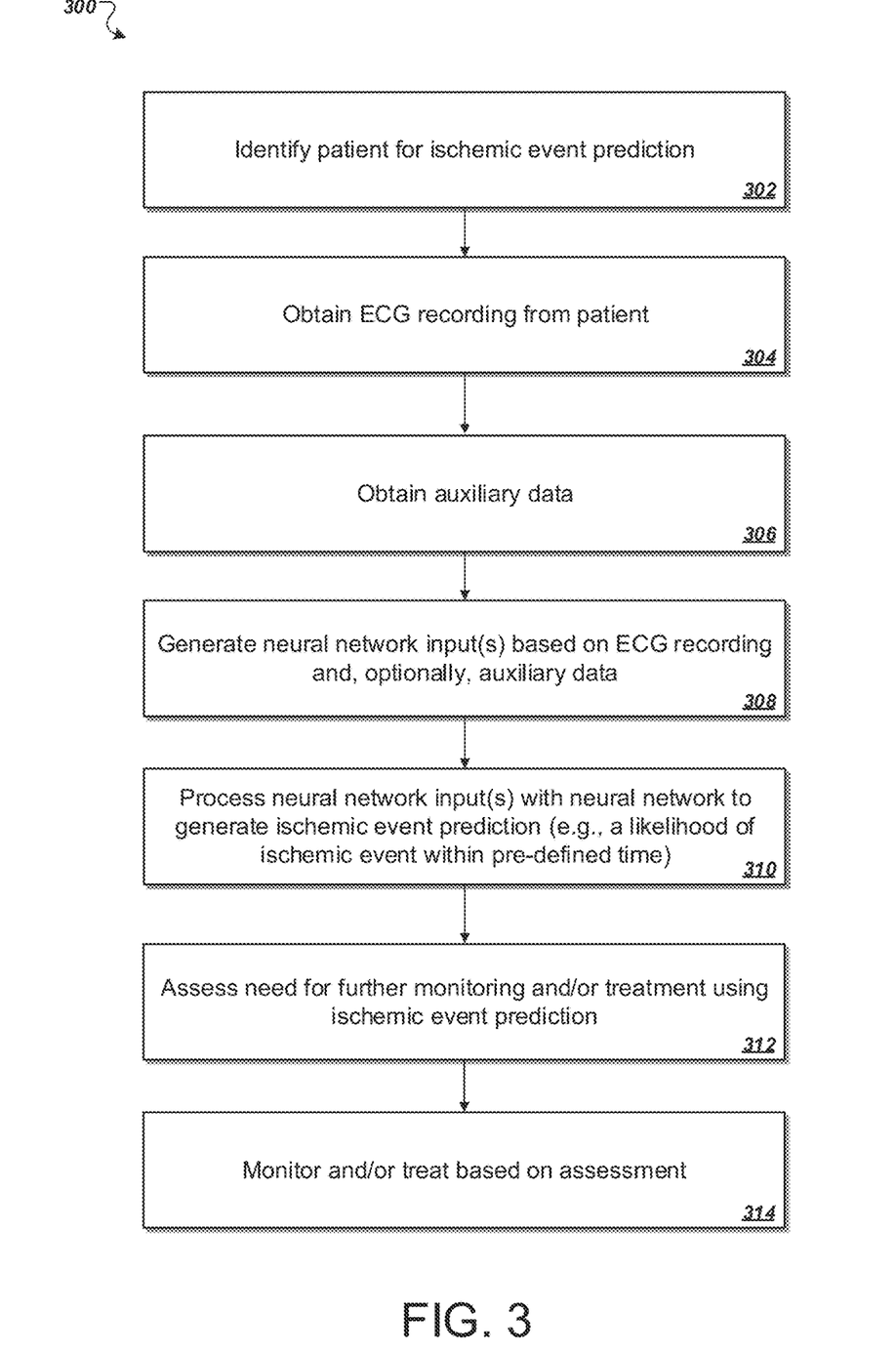
FIG. 3 is a flowchart of an example process for recording an ECG of a patient and processing data representative of the recording to predict an ischemic event.

FIG. 3 is a flowchart of an example process 300 for recording an ECG of a patient and processing data representative of the recording to generate an ischemic event prediction. The ischemic event prediction can be used by a physician or other human or automated decision-maker to determine or recommend a monitoring and/or treatment regime for the patient. A patient is identified to predict a potential ischemic event (302). An ECG recording is obtained from the patient (304). The ECG recording may be obtained using a single-lead or multi-lead (e.g., standard 12-lead) ECG. Optionally, auxiliary data such as morphological features for the ECG and/or patient profile data can be obtained (306). The system generates neural network inputs based on the ECG recording and the auxiliary data, if available (308). The ischemic event prediction neural network processes the neural network inputs to generate the ischemic event prediction (310). The ischemic event prediction can indicate a likelihood that the patient will experience the ischemic event within a pre-defined time interval from a time when the ECG recording was made. A physician or other healthcare provider can assess the need for further monitoring or treatment of the patient's condition based on the ischemic event prediction (312). For example, to lower the risk of ischemic event once the patient has been identified as likely having ischemic event, medication and/or other treatment may be prescribed to the patient. Additionally, the patient may undergo longer-term continuous monitoring to identify actual episodes of ischemic event (314).

Figure 4:
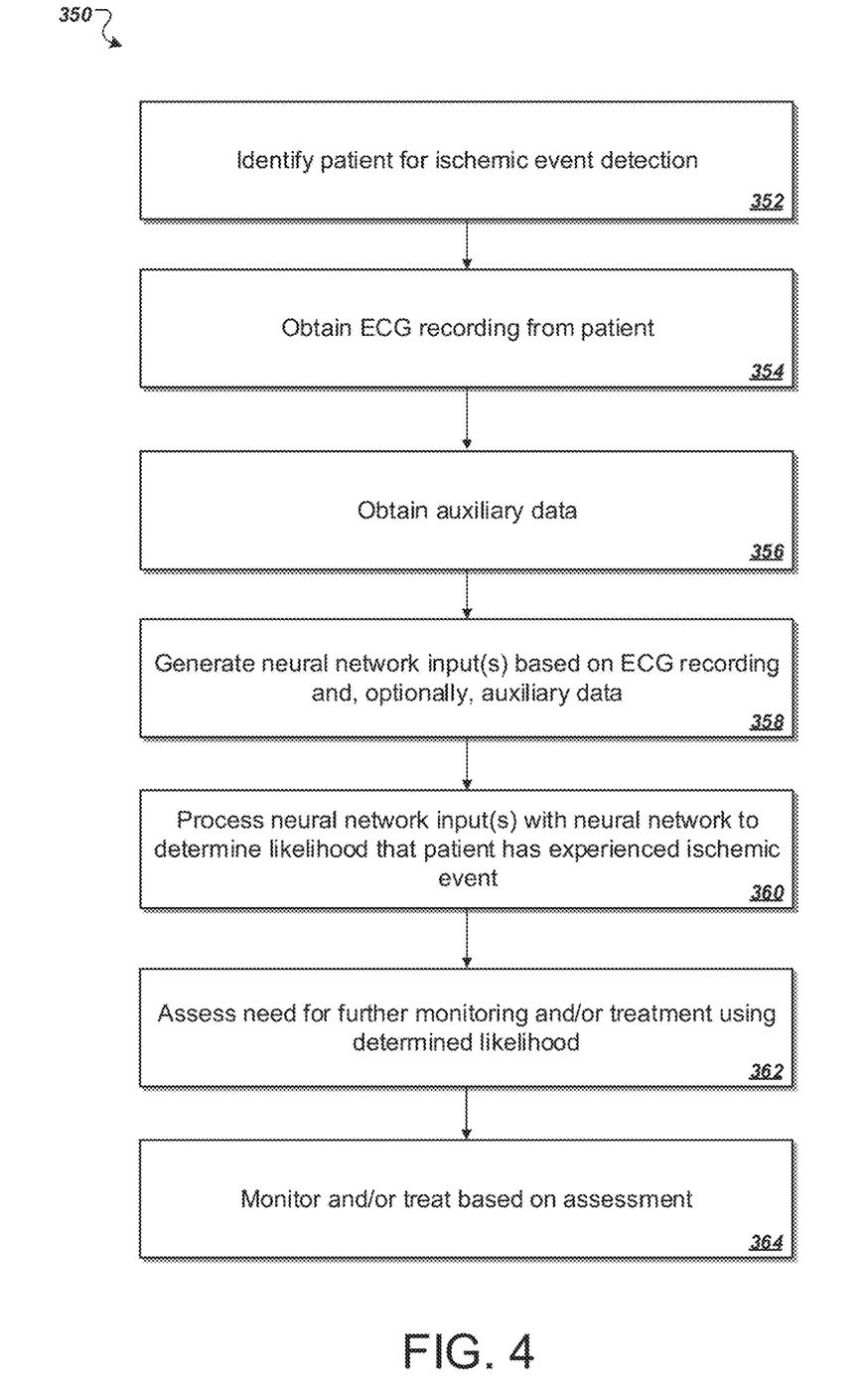
FIG. 4 is a flowchart of an example process for recording an ECG of a patient and processing data representative of the recording to diagnose an ischemic event.

FIG. 4 is a flowchart of an example process 350 for recording an ECG of a patient and processing data representative of the recording to detect an ischemic event. The ischemic event detection can be used by a physician or other human or automated decision-maker to determine whether the patient has actually suffered an ischemic event although the patient did not appear to have such an ischemic event. The ischemic event detection can also be used to recommend a monitoring and/or treatment regime for the patient. A patient is identified to detect an actual ischemic event (352). An ECG recording is obtained from the patient (354). The ECG recording may be obtained using a single-lead or multi-lead (e.g., standard 12-lead) ECG. Optionally, auxiliary data such as morphological features for the ECG and/or patient profile data can be obtained (356). The system generates neural network inputs based on the ECG recording and the auxiliary data, if available (358). The ischemic event detection neural network processes the neural network inputs to generate the ischemic event detection (360). The ischemic event detection can indicate a likelihood that the patient experienced the ischemic event. A physician or other healthcare provider can assess the need for further monitoring or treatment of the patient's condition based on the ischemic event prediction (362). For example, to lower the risk of ischemic event once the patient has been identified as having had an ischemic event, medication and/or other treatment may be prescribed to the patient. Additionally, the patient may undergo longer-term continuous monitoring to identify any potential ischemic event in the future (314).

Figure 5:
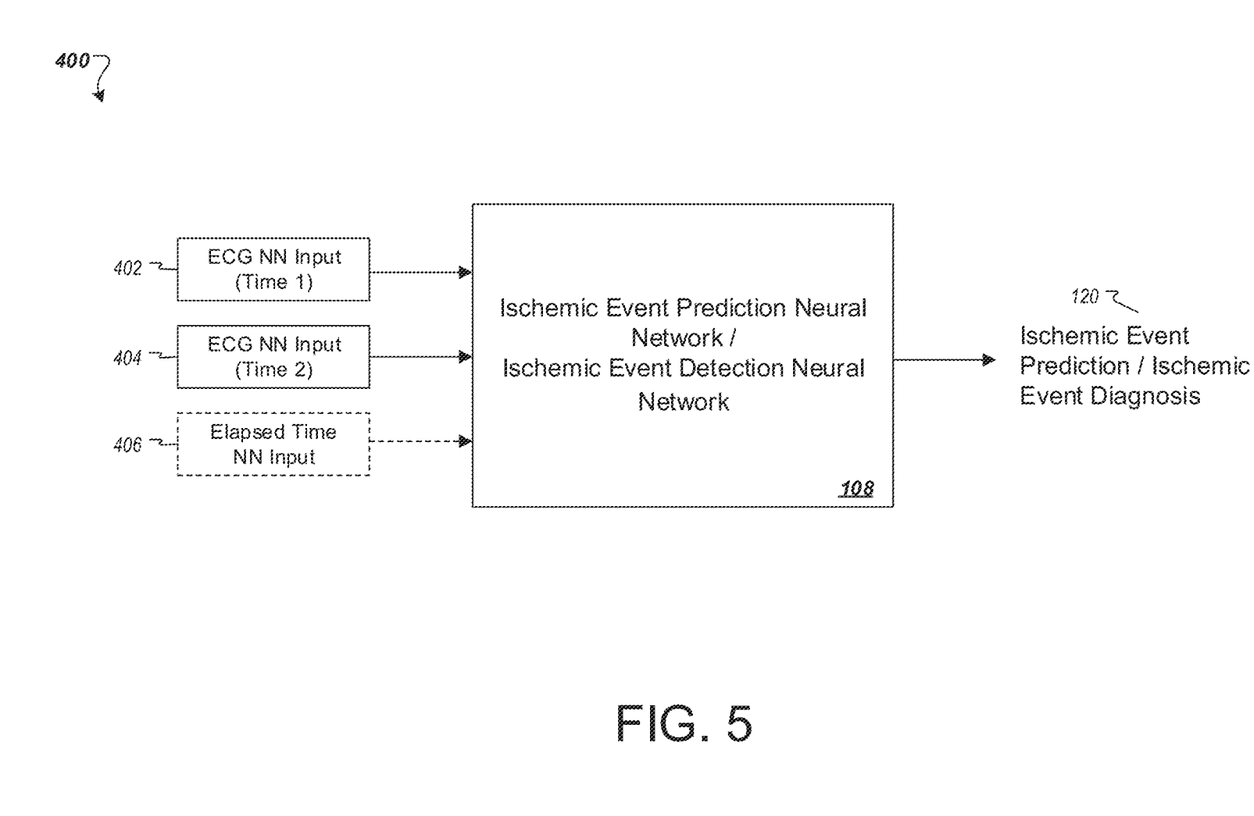
FIG. 5 is a diagram of an example neural network that processes temporally spaced ECG recordings of a patient to generate an ischemic event prediction or an ischemic event detection for the patient based in part on features representing differences between the ECG recordings over time.

FIG. 5 is a diagram of an example neural network system 400 that processes temporally spaced ECG recordings of a patient to generate an ischemic event prediction or detection for the patient based in part on features representing differences between the ECG recordings over time. Here, the ischemic event prediction/detection neural network 108 is configured to process a first neural network input 402 representing an ECG recording of the patient at a first time (e.g., over a short time interval such as less than or equal to 30, 20, 15, 10, or 5 seconds) and a second neural network input 404 representing a second ECG recording of the patient at a second time (e.g., over a short time interval such as less than or equal to 30, 20, 15, 10, or 5 seconds). In some cases, the neural network 108 further processes a neural network input 406 that indicates an amount of elapsed time between the times the first and second ECG recordings representing in inputs 402 and 404 were recorded. For example, the input 406 can indicate that the ECG recordings were taken a number of hours, days, weeks, months, or years apart from each other. The neural network 108 can then process each of the inputs 402, 404, and 406 to generate an ischemic event prediction or detection 120.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" refers to data processing hardware and encompasses all kinds of apparatus, devices, and machines for processing data, including by way of example a programmable processor, a computer, or multiple processors or computers. The apparatus can also be, or further include, off-the-shelf or custom-made parallel processing subsystems, e.g., a GPU or another kind of special-purpose processing subsystem. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for diagnosing an ischemic event for a subject mammal, comprising:
   receiving, by an ischemic event detection neural network, a neural network input, the neural network input representing an electrocardiogram (ECG) recording of the subject mammal that was recorded over a period of time, the subject mammal having no appearance of the ischemic event over the period of time; and
   processing, with the ischemic event detection neural network, the neural network input to determine a likelihood that the subject mammal experienced the ischemic event.

2. The method of claim 1, wherein the ischemic event detection neural network is trained on ECG training data that includes a plurality of ECG training samples, each ECG training sample including an ECG recording of a given mammal and a label indicating whether the given mammal is known to have experienced an ischemic event.

3. The method of claim 2, wherein the given mammals for particular ones of the ECG training samples are different from each other.

4. The method of claim 2, wherein, for each of at least a subset of the ECG training samples, the label for the training sample or a second label for the training sample indicates an amount of time that elapsed between a time when the ECG recording for the training sample was made and a time when the given mammal for the training sample experienced an ischemic event.

5. The method of claim 2, wherein the ECG recording of the subject mammal was recorded over a first time interval, and the method further comprises:
   obtaining a second neural network input, the second neural network input representing a second ECG recording of the subject mammal that was recorded over a second time interval, the first time interval and the second time interval separated by a third time interval; and
   processing the first neural network input along with the second neural network input with the ischemic event detection neural network to determine the likelihood that the subject mammal experienced the ischemic event.

6. The method of claim 1, wherein the ischemic event is a transient ischemic attack (TIA).

7. The method of claim 1, wherein the ischemic event is a stroke.

* * * * *